United States Patent [19]
Riazzi et al.

[11] Patent Number: 5,406,945
[45] Date of Patent: Apr. 18, 1995

[54] BIOMEDICAL ELECTRODE HAVING A SECURED ONE-PIECE CONDUCTIVE TERMINAL

[75] Inventors: Timothy J. Riazzi, Kettering; Michael L. Wolf, West Milton; Michael J. Allaire, Cincinnati, all of Ohio

[73] Assignee: NDM Acquisition Corp., Minneapolis, Minn.

[21] Appl. No.: 66,716

[22] Filed: May 24, 1993

[51] Int. Cl.⁶ .............. A61B 5/0402; A61B 5/0488; A61N 1/04
[52] U.S. Cl. ..................... 128/641; 607/149; 607/152; 607/153
[58] Field of Search ............... 128/640, 641; 607/149, 607/152, 153

[56] References Cited
U.S. PATENT DOCUMENTS

| | | |
|---|---|---|
| 3,989,035 | 11/1976 | Zuehlsdorff. |
| 4,066,078 | 1/1978 | Berg ........................... 128/641 |
| 4,580,339 | 4/1986 | Ioffe ............................ 128/641 |
| 4,694,833 | 9/1987 | Strand ........................ 128/640 |
| 4,777,954 | 10/1988 | Keusch et al. ............. 128/641 |
| 5,042,144 | 8/1991 | Shimada et al. ............ 128/641 |

FOREIGN PATENT DOCUMENTS

| | | |
|---|---|---|
| 0142372A1 | 5/1985 | European Pat. Off. . |
| 0255241A3 | 2/1988 | European Pat. Off. . |
| WO81/02097 | 8/1981 | WIPO . |

*Primary Examiner*—Lee S. Cohen
*Attorney, Agent, or Firm*—Killworth, Gottman, Hagan & Schaeff

[57] ABSTRACT

A disposable biomedical electrode having a one-piece terminal secured therein without washers, retaining rings or other securement means is provided. The electrode also includes an electrolytic gel which exhibits greater patient comfort without any decrease in electrical performance. The gel layer is preferably a hydrogel material formed from an aqueous mixture of polyhydric alcohol, aliphatic diisocyanate terminated prepolymer, polyethylene oxide based polyamine, and sodium chloride.

11 Claims, 5 Drawing Sheets

BIOMEDICAL ELECTRODE HAVING A SECURED ONE-PIECE CONDUCTIVE TERMINAL

BACKGROUND OF THE INVENTION

The invention relates to the field of disposable biomedical electrodes for establishing an electrical connection between the skin of the human anatomy and an electromedical apparatus such as a high impedance electromyograph, electrocardiograph, electrostimulator for pain relief and the like. More specifically, the present invention is directed to a disposable biomedical electrode having a secured one-piece conductive terminal which is formed using less material, resulting in decreased manufacturing expenses. The biomedical electrode can also include an improved electrolytic gel which provides more comfort for the patient while maintaining electrical performance.

Many types of disposable biomedical electrodes have been introduced in recent years. Typically they comprise: (1) a metallic or electrically-conductive carbon terminal member having means for electrical connection to an electromedical apparatus such as an electrocardiograph; (2) an adhesive tape or pad for holding the terminal member in place on the skin; and (3) an electrically-conductive, conformable interfacing material such as an electrolyte gel or paste over the surface of the terminal member which contacts the skin to reduce skin impedance and to improve electrical contact between the skinland the terminal member.

Disposable biomedical electrodes have been improved in the last few years by the introduction of electrically-conductive, pressure-sensitive adhesives to replace conventional electrolyte gels and creams. Such gels were generally unpleasant to use and, because of their high water content, required elaborate packaging to prevent "dry-out" problems. The electrically-conductive, pressure-sensitive adhesives are not as comfortable for patients when attached to their skin in that they do not provide a soothing or moist feeling and hair tends to be torn away from the patient's body upon removal of the electrode. It would be desirable, therefore, to have a disposable biomedical electrode which includes an electrolyte gel which is more comfortable for the patient, yet does not experience "dry-out" problems or reduced electrical performance.

For ease of connection to the lead wire of an electromedical device, the terminal member of many disposable biomedical electrodes is formed in the shape of the male portion of a snap fastener adapted to engage the female portion of the snap fastener attached to the lead wire of the electromedical device. Such a terminal member comprises a flat, circular portion and a knob-like projection extending perpendicularly therefrom. A one-piece terminal member of this type is difficult to anchor securely to the adhesive pad. If the terminal member is not securely anchored to the other components of the disposable electrode, it may pull out when force is applied to disconnect the terminal member from the female portion of the snap fastener.

To avoid this problem, a two-piece terminal member is typically used in the art comprising a so-called "stud and eyelet" arrangement. The stud comprises a flat circular portion and a pin-like member extending perpendicularly therefrom. The stud is inserted into an eyelet comprising a hollow knob having a circular base. Adhesive tape or a stiffening piece used to reinforce the adhesive tape is sandwiched between the stud and the eyelet. After the stud is inserted into the eyelet, the eyelet is crimped at its neck to ensure good electrical contact between the stud and eyelet and to anchor the adhesive tape or stiffening piece securely. Alternatively, the stud can be friction- fitted within the eyelet without crimping. The two-piece terminal member as described above suffers from a number of disadvantages including potential corrosion problems if the stud and eyelet are made from dissimilar metals, high electrical resistance between the stud and eyelet, and increased difficulty and cost of manufacturing.

Because of the disadvantages associated with the two-piece terminal member, particularly its high cost, a number of attempts have been made to solve the anchoring problems encountered with one-piece terminal members so that the latter might be more suitable for disposable biomedical electrodes. For example, a retaining ring which fits over the projecting portion of the terminal member to mechanically secure the adhesive tape to the flat base portion of the terminal member has been used in the past. Further, Corasanti, U.S. Pat. No. 4,029,086, describes a disposable biomedical electrode having a one-piece terminal member in which the projecting portion thereof contains a ridge over which a washer is snapped to secure the terminal member to the adhesive pad.

In general, the prior art methods of anchoring one-piece terminal members to the other components of the electrodes have involved a friction-fit washer or retaining ring which is mechanically biased against the stem of the knob-like projection of the terminal member. Although such methods of anchoring generally produce satisfactory anchoring of the terminal member to the electrode, they complicate the manufacture of the electrode and increase its cost. Thus, it would also be desirable to have a biomedical electrode with a design that includes a one-piece terminal member secured therein without washers, retaining rings and the like which complicate the manufacturing scheme.

Accordingly, there is need in the art for a disposable biomedical electrode which includes an electrolyte gel that is comfortable for the patient but does not experience the aforementioned "dry-out" problems or decreased electrical performance of prior devices. Additionally, there is a need for such a biomedical electrode which includes a one-piece terminal member secured therein without the need for washers, retaining rings and the like which complicate the manufacturing of such electrodes and thereby increase their cost.

SUMMARY OF THE INVENTION

The present invention meets the above-identified needs by providing a disposable biomedical electrode having a one-piece terminal member secured therein without washers, retaining rings or other securement means, thereby decreasing the material requirements and manufacturing costs for the electrode. The electrode of the invention can also include an electrolytic gel which improves patient comfort without any decrease in electrical performance. Thus, for example, several of the electrodes of the invention can be comfortably attached to a patient requiring electrocardiographic monitoring, and the patient will experience a soothing and moist feeling as opposed to an excessively sticky feeling. Moreover, upon removal of the electrodes of the invention, it is less likely that hair will be torn or otherwise removed from the patient's body than with prior electrodes having pressure-sensitive or conductive adhesive-based gels.

In accordance with one aspect of the invention, a disposable biomedical electrode is provided. The biomedical electrode comprises an electrolytic gel layer having first and second sides wherein the first side is adapted to contact a patient. Preferably, the second side of the gel layer includes a support layer for the gel layer. An anchoring layer is included in which each side may be coated with an adhesive. The first side of the anchoring layer is secured to the support layer on the second side of the gel layer. Further, the electrode includes a conductive one-piece terminal having a base portion integrally joined to a stud member, wherein the base portion is centrally mounted to the second side of the anchoring layer.

A preferred electrode construction also comprises a reinforcing strip having a first opening correspondingly sized with the stud member of the terminal, wherein the reinforcing strip is mounted over the terminal such that the stud member protrudes through the first opening and the base portion is held against the second side of the anchoring layer. Finally, the electrode includes a top layer having first and second sides and a second opening correspondingly sized with the stud member of the terminal. The second side of the top layer has first and second ends and a patient-contact adhesive coating. The top layer is adhesively mounted onto the reinforcing strip and the anchoring layer such that the stud member protrudes through the second opening, and the first and second ends of the second side of the top layer are capable of being secured to the patient.

In accordance with another aspect of the invention, a disposable biomedical electrode is provided in which the electrolytic gel layer does not require a support layer. Specifically, the biomedical electrode comprises an electrolytic gel layer having first and second sides wherein the first side is adapted to contact a patient. An anchoring layer is included in which each side may be coated with an adhesive. The first side of the anchoring layer is secured to the second side of the gel layer. Further, a conductive terminal is included which has a base portion integrally joined to a stud member, wherein the base portion is centrally mounted to the second side of the anchoring layer.

Alternatively, the anchoring layer of the above-discussed embodiments may be replaced by two anchoring strips. In the embodiment in which a support layer is used, the anchoring strips are secured to the support layer at opposite ends of the second side of the gel layer. Where no support layer is employed, the anchoring strips are secured to the second side of the gel layer at opposite ends.

Preferably, the electrode also includes a reinforcing strip having a first opening correspondingly sized with the stud member of the terminal. The reinforcing strip is mounted over the terminal such that the stud member protrudes through the opening and the base portion is held against the second side of the anchoring layer. If anchoring strips are used in place of an anchoring layer, the base portion of the conductive terminal is held against the second side of the support layer. Finally, a top layer is included which has first and second sides and a second opening correspondingly sized with the stud member of the terminal, wherein the second side of the top layer has first and second ends and a patient-contact adhesive coating. The top layer is adhesively mounted onto the reinforcing strip and the anchoring layer/strips such that the stud member protrudes through the second opening and the first and second ends of the second side are capable of being secured to the patient.

In accordance with another aspect of the present invention, a disposable biomedical electrode is provided in which no separate reinforcing strip is required. The biomedical electrode comprises an electrolytic gel layer having first and second sides wherein the first side is adapted to contact a patient. A conductive terminal is included which has a base portion integrally joined to a stud member, wherein the base portion is centrally mounted to the second side of the gel layer. The electrode also includes an anchoring patch having a first opening correspondingly sized with the stud member of the terminal, wherein the anchoring patch is mounted over the terminal such that the stud member protrudes through the opening and the base portion is held against the second side of the gel layer. The electrode comprises a top layer having first and second sides and a second opening correspondingly sized with the stud member of the terminal. The second side of the top layer has a patient-contact adhesive coating. The top layer is adhesively mounted onto the anchoring patch such that the stud member protrudes through the second opening and the periphery of the second side of the top layer is capable of being secured to the patient. Finally, the electrode includes a cap portion adapted for attachment over the stud member of the terminal. This cap portion is positioned on the first side of the top layer, over the second opening.

In another embodiment of the invention, the disposable biomedical electrode includes an electrolytic gel which provides several advantages over those used in the past, such as improved comfort for the patient and minimal "dry-out" problems. More particularly, the preferred gel layer is a hydrogel material formed from an aqueous mixture of polyhydric alcohol, aliphatic diisocyanate-terminated prepolymer, polyethylene oxide-based polyamine, and sodium chloride. In a preferred embodiment, the hydrogel material is formed from an aqueous mixture comprising: (a) from about 0% to about 90% by weight polyhydric alcohol; (b) from about 6% to about 60% by weight aliphatic diisocyanate-terminated prepolymer; (c) from about 4% to about 40% by weight polyethylene oxide-based polyamine; (d) 0% to about 2% by weight sodium chloride; and (e) the balance water.

Accordingly, it is a feature of the present invention to provide a disposable biomedical electrode which includes an electrolyte gel which is more comfortable for the patient and, yet, does not experience the "dry-out" problems or sacrifice electrical performance; and, it is also a feature of the invention to provide such a biomedical electrode which includes a one-piece terminal member secured therein without washers, retaining rings and the like which complicate the manufacturing scheme, and thereby increase its cost. Other features and advantages of the invention will be apparent from the following detailed description, the accompanying drawings, and the appended claims.

DETAILED DESCRIPTION OF THE PREFERRED EMBODIMENTS

Figure 1:
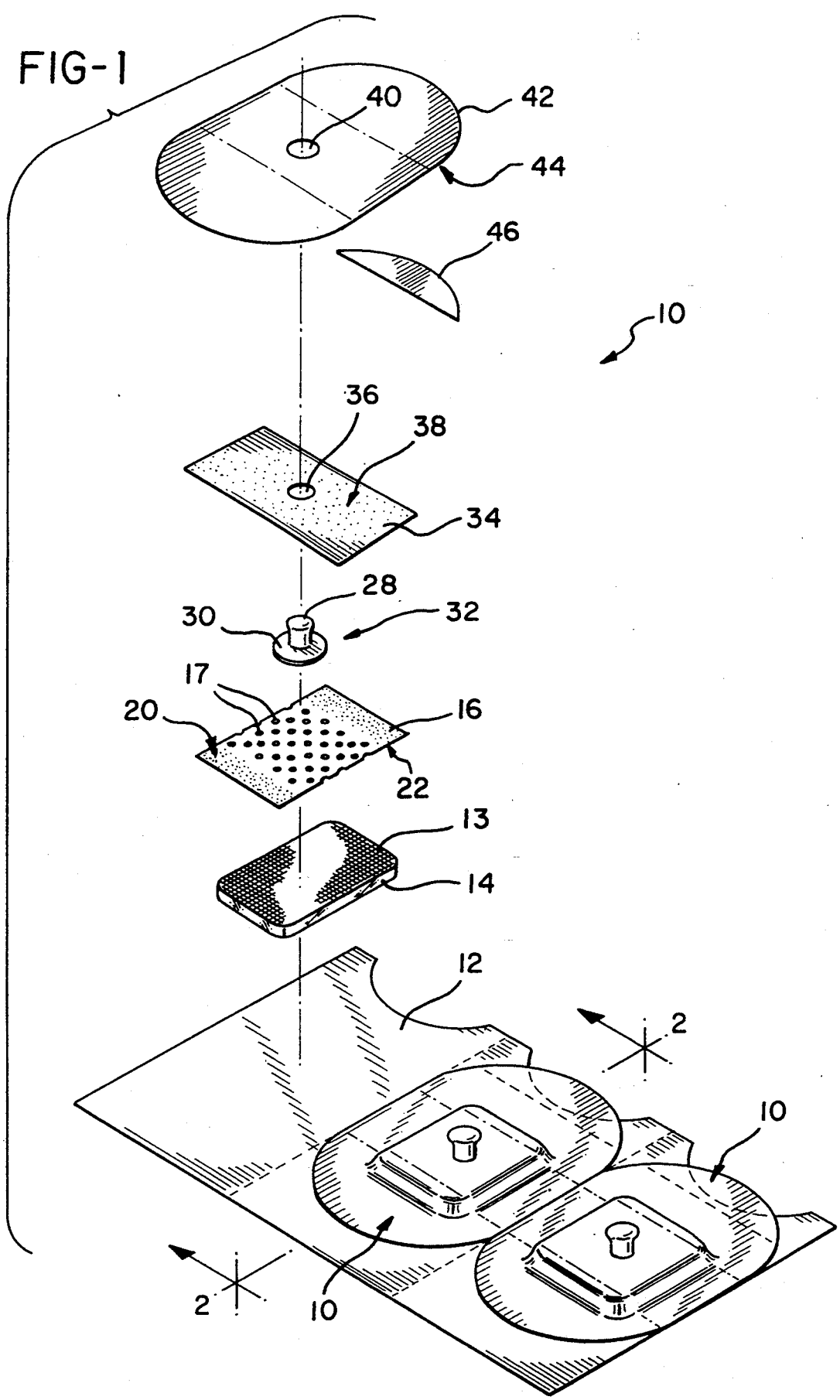
FIG. 1 is an exploded view of one embodiment of the disposable biomedical electrode of the invention.
Figure 2:
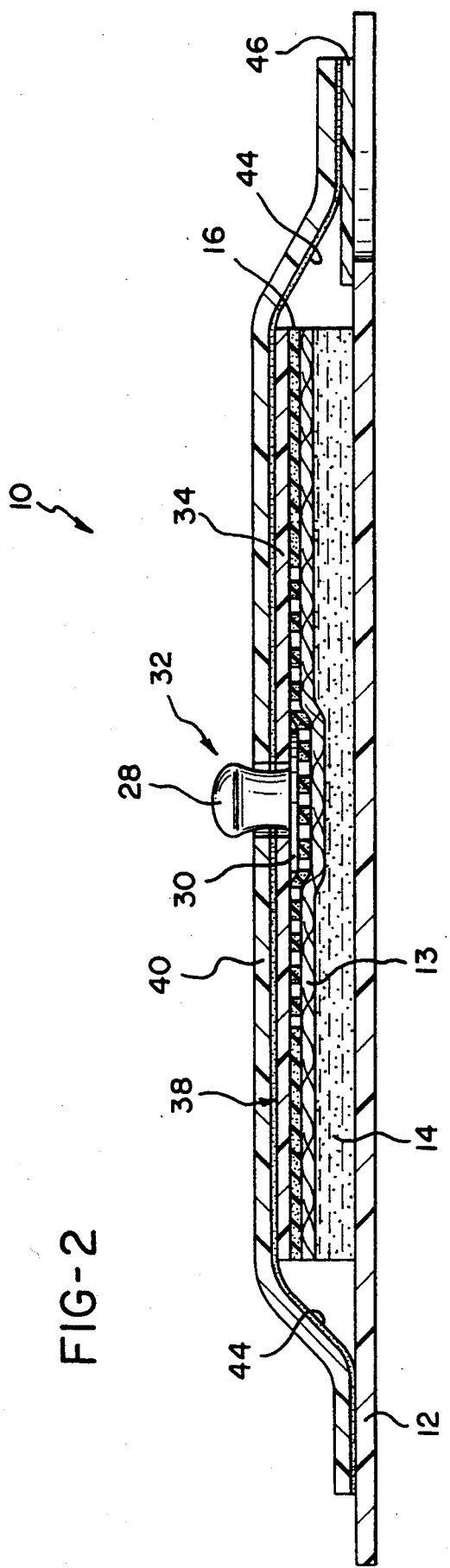
FIG. 2 is an enlarged cross-sectional view taken along view line 2—2 in FIG. 1 of the electrode of the invention.

Reference is now made collectively to FIGS. 1 and 2, both of which illustrate an embodiment of the disposable biomedical electrode of the present invention. FIG. 1 is an exploded perspective view of a disposable biomedical electrode 10 and several other identical electrodes as they are mounted on a release liner 12 prior to use. FIG. 2 is an enlarged cross-sectional view of the electrode 10 taken along view line 2—2 in FIG. 1. As seen in FIGS. 1 and 2, the electrode 10 comprises an electrolytic gel layer 14 with an optional support layer 13 disposed within. The support layer 13 adds additional support to the gel layer 14. Preferably, the electrode 10 includes an anchoring layer 16, each side of which may be coated with an adhesive layer individually referenced as adhesive layers 20 and 22.

The anchoring layer 16 is formed of a porous material having sufficient porosity such that the anchoring layer 16 can be secured to the gel layer 14 without an adhesive. It has been found that when the anchoring layer 16 is formed of sufficiently porous material, it readily adheres directly to most conventional conductive adhesives and electrolytic hydrogels, as well as to hydrogels of the nature described herein. Other materials do not adhere directly to electrolytic gels and, thus, require an adhesive coating in order to provide a means by which the anchoring layer 16 can be secured to the gel layer 14. The anchoring layer 16, however, possesses sufficient porosity to eliminate the necessity of an adhesive and a support layer, thereby reducing the cost of the electrode 10 by reducing material and manufacturing expenses.

Preferably, the anchoring layer 16 is formed of a porous material comprising a foam material including silica and a polyolefin, wherein the porous material has a porosity ranging from about 30% to about 80%. The preferred porous material is a microporous synthetic sheet commercially available from PPG Industries, Inc., under the trademark Teslin ®. Those skilled in the art will understand that the extent to which the porous material must be porous will depend upon the particular gel material chosen to form the gel layer 14. Further, those skilled in the art will appreciate that sufficiently porous materials other than those described herein may be used without departing from the scope of the invention.

Further, the electrode 10 includes a conductive terminal 32 comprising a base portion 30 integrally joined to a stud member 28, wherein the base portion 30 is centrally mounted to the upper surface or side of the anchoring layer 16. The anchoring layer 16 is secured to the upper surface of the gel layer 14. In order to allow electrical contact between the terminal 32 and the electrolytic gel layer 14, the anchoring layer 16 is perforated with a series of holes 17.

The preferred electrode 10 also comprises a reinforcing strip 34 having an opening 36 correspondingly sized with the stud member 28 of the terminal 32. The reinforcing strip 34 is mounted over the terminal 32 such that the stud member 28 protrudes through the opening 36 and the base portion 30 is held against the upper surface of the anchoring layer 16. As a result of the reinforcing strip 34 being mounted in this manner, the terminal 32 is securely attached to the electrode and is prevented from wiggling or otherwise moving which could alter the electrical signal transmitted and cause inaccurate medical test data. Optionally, the reinforcing strip 34 can include an adhesive coating 38 to facilitate securement thereof in the electrode 10.

Additionally, the electrode 10 includes a top layer 42 having an opening 40 correspondingly sized with the stud member 28 of the terminal 32. Preferably, the lower side or surface of the top layer 42 has a patient-contact adhesive coating 44. The top layer 42 is adhesively mounted onto the reinforcing strip 34 and the anchoring layer 16 such that the stud member 28 protrudes through the opening 40 and the ends of the lower side of the top layer 42 are capable of being secured to the patient. In this way, all of the individual components of the electrode 10 are easily secured together without the need for any retaining means such as eyelets, washers, and the like.

Additional advantages are achieved by the present invention with the use of the preferred gel layer 14. Specifically, it is preferable to have a gel layer 14 which is a hydrogel material formed from an aqueous mixture of polyhydric alcohol, an aliphatic diisocyanate-terminated prepolymer, polyethylene oxide-based diamine, and sodium chloride. It should be understood that hydrogels other than those described herein which have the desired properties may be used as the gel layer 14 without departing from the scope of the invention. Preferably, the polyhydric alcohol is selected from the group consisting of polypropylene glycol, polyethylene glycol and glycerine. The resulting hydrogel material is an electrically conductive and highly absorbent material capable of retaining large amounts of fluid, thereby rendering it very moist and soothing. By forming the hydrogel material from the aforementioned aqueous mixture, it remains intact and experiences minimal "dry-out" problems, even over extended storage periods.

Moreover, the hydrogel material used to form the gel layer 14 does not adhere or stick to the patient's body, thereby allowing for easy removal of the electrode 10 substantially as a single piece and without adhering to the patient's hair. Additionally, the biocompatibility of the hydrogel material is extremely favorable and, therefore, provides a biocompatible, nonirritating, fluid-absorbing, bacterial-protective, cushioning, skin-like media in and over the patient's skin during medical testing.

Those skilled in the art will appreciate that a wide variety of aliphatic diisocyanates may be used in accordance with the invention including but not limited to hexamethylene diisocyanate, isophoronediisocyanate, tetramethylene diisocyanate and decamethylene diisocyanate. The preferred aliphatic diisocyanate-terminated prepolymer, however, is an isophoronediisocyanate-terminated prepolymer based on polyols containing more than about 40% polyethylene oxide and having an isocyanate content of about 3% by weight. The molecular weight of the isophoronediisocyanate-terminated prepolymer is preferably in a range from about 1500 to about 8000 and, most preferably, from about 4000 to about 5000. The polyethylene oxide-based polyamine is preferably a polyethylene oxide-based diamine having a molecular weight in a range from about 200 to about 6000 and, most preferably, about 2000. It is also preferable that the aliphatic diisocyanate-terminated prepolymer and the polyethylene oxide-based polyamine have a stoichiometric ratio of about 1:1. Those skilled in the art will appreciate that all of the constituents of the preferred hydrogel material may be readily synthesized or purchased commercially, with neither method being preferred over the other.

It has been found that a more preferred hydrogel material is formed from an aqueous mixture including from about 0% to about 90% by weight polyhydric alcohol; from about 6% to about 60% by weight aliphatic diisocyanate-terminated prepolymer; from about 4% to about 40% by weight polyethylene oxide-based polyamine; up to about 2% by weight sodium chloride; and the balance water. A more preferred hydrogel composition for forming the hydrogel material is formed from a mixture comprising from about 15% to about 30% by weight polypropylene glycol; from about 8% to about 14% by weight isophoronediisocyanate-terminated prepolymer; from about 5% to about 10% by weight polyethylene oxide-based diamine; up to about 1% by weight sodium chloride; and the balance water. Most preferably, the hydrogel material is formed from a mixture comprising: (a) from about 16% to 17% by weight polypropylene glycol; (b) from about 10% to 12% by weight isophoronediisocyanate-terminated prepolymer; (c) from about 7% to 9% by weight polyethylene oxide-based diamine; (d) from about 0.5% to 1% by weight sodium chloride; and (e) the balance water.

FIGS. 1 and 2 also illustrate an optional conventional release tab 46 which can be secured to one end of the lower side of the top layer 42. When the release tab 46 is used in conjunction with the release liner 12, the user, for example a nurse, can simply peel the electrode 10 away from liner 12 by grasping the release tab 46. Thereafter, the user can remove the release tab 46 and mount the electrode 10 on the patient. Such techniques are conventional and well known. The release tab 46 and the release liner 12 may be composed of any one of a number of materials, such as silicone-coated paper or others.

Preferably, the support layer 13 is formed from a material selected from the group consisting of fabrics, natural fibers, synthetic fibers, cellulose derivatives and combinations thereof. Most preferably, the support layer 13 comprises a scrim material. The reinforcing strip 34 and the top layer 42 may be formed of a polymeric film material such as polyethylene, polyester and the like, as well as other flexible semi-rigid materials. In addition, the top layer 42 can be formed of a foam, film or cloth material. The terminal 32 is preferably comprised of metal or is provided with a metallized outer layer, but it can comprise other materials such as conductive carbon interdispersed in a thermoset polymer. Those skilled in the art should appreciate that materials other than those described herein can be used to form the various components without departing from the scope of the invention.

Figure 3:
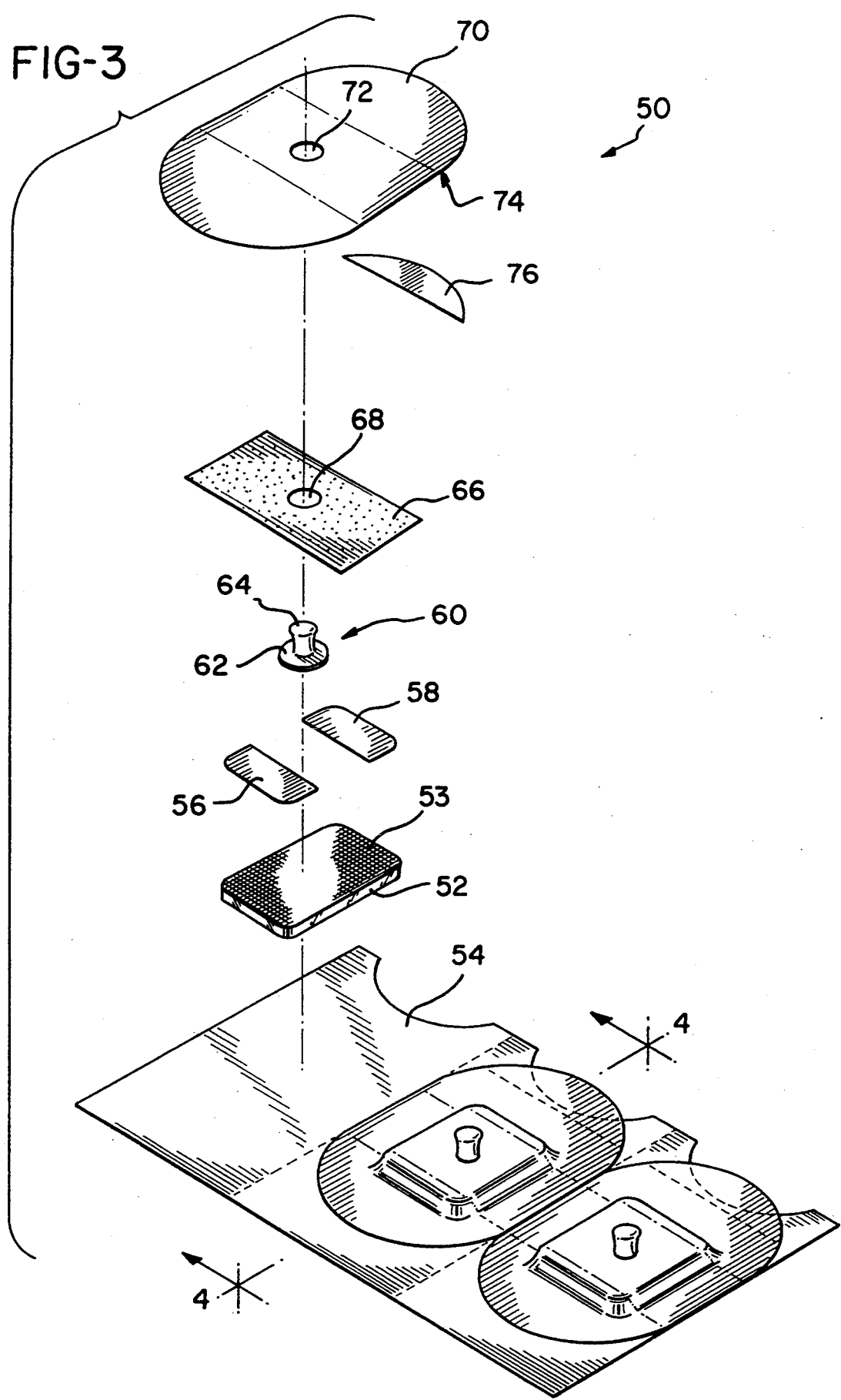
FIG. 3 is an exploded view of another embodiment of the biomedical electrode of the invention.
Figure 4:
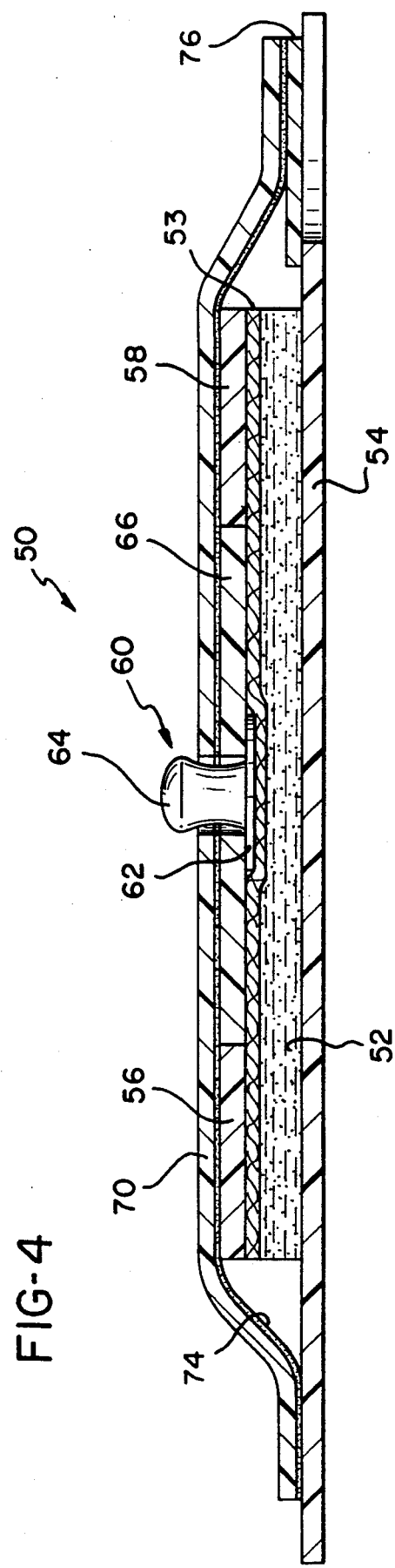
FIG. 4 is a cross-sectional view taken along view line 4—4 in FIG. 3 of the electrode shown therein.

Reference is now made collectively to FIGS. 3 and 4 in which another embodiment of the invention is depicted. FIG. 3 illustrates a disposable biomedical electrode 50 in accordance with the invention. FIG. 4 shows a cross-sectional view taken along view line 4—4 in FIG. 3 of the electrode 50. The electrode 50 possesses the same advantages as the electrode 10 described above, but includes anchoring strips 56 and 58 in place of anchoring layer 16 of FIGS. 1 and 2. Specifically, the electrode 50 comprises an electrolytic gel layer 52 which is formed from the same materials as the gel layer 14 described above. The electrode 50 further includes a support layer 53 either on the upper surface of gel layer 52 or disposed within gel layer 52. As seen in FIGS. 3 and 4, the gel layer 52 can optionally be mounted on a release liner 54 prior to use.

Anchoring strips 56 and 58 are included which are preferably formed of the same material as the anchoring layer 16 described above. A conductive terminal 60 having a base portion 62 integrally joined to a stud member 64 is centrally mounted to the upper side of gel layer 52 and between anchoring strips 56 and 58. The electrode 50 also includes a reinforcing strip 66 having an opening 68 correspondingly sized with the stud member 64 of the terminal 60. The reinforcing strip 66 is mounted over the terminal 60 such that the stud member 64 protrudes through the opening 68 and the base portion 62 is held against the upper side or surface of gel layer 52. Finally, a top layer 70 is included which has an opening 72 correspondingly sized with the stud member 64 of the terminal 60.

Preferably, the top layer 70 has a patient-contact adhesive coating 74 conducive for attachment to patients requiring medical diagnostic testing of the nature described previously. The top layer 70 is adhesively mounted by way of the adhesive coating 74 onto the reinforcing strip 66 and the anchoring strips 56 and 58 such that the stud member 64 protrudes through the opening 72 and the ends of the top layer 70 are capable of being secured to the patient. As with the electrode 10, a release tab 76 can be included to facilitate removal of the electrode 50 from the release liner 54. It should be understood that all of the materials used to make the various components for the electrode 10 can be used for the similar components in the electrode 50. For example, the hydrogel material and associated formulations used in gel layer 14 of electrode 10 are preferably used to form the gel layer 52 in the electrode 50.

Figure 5:
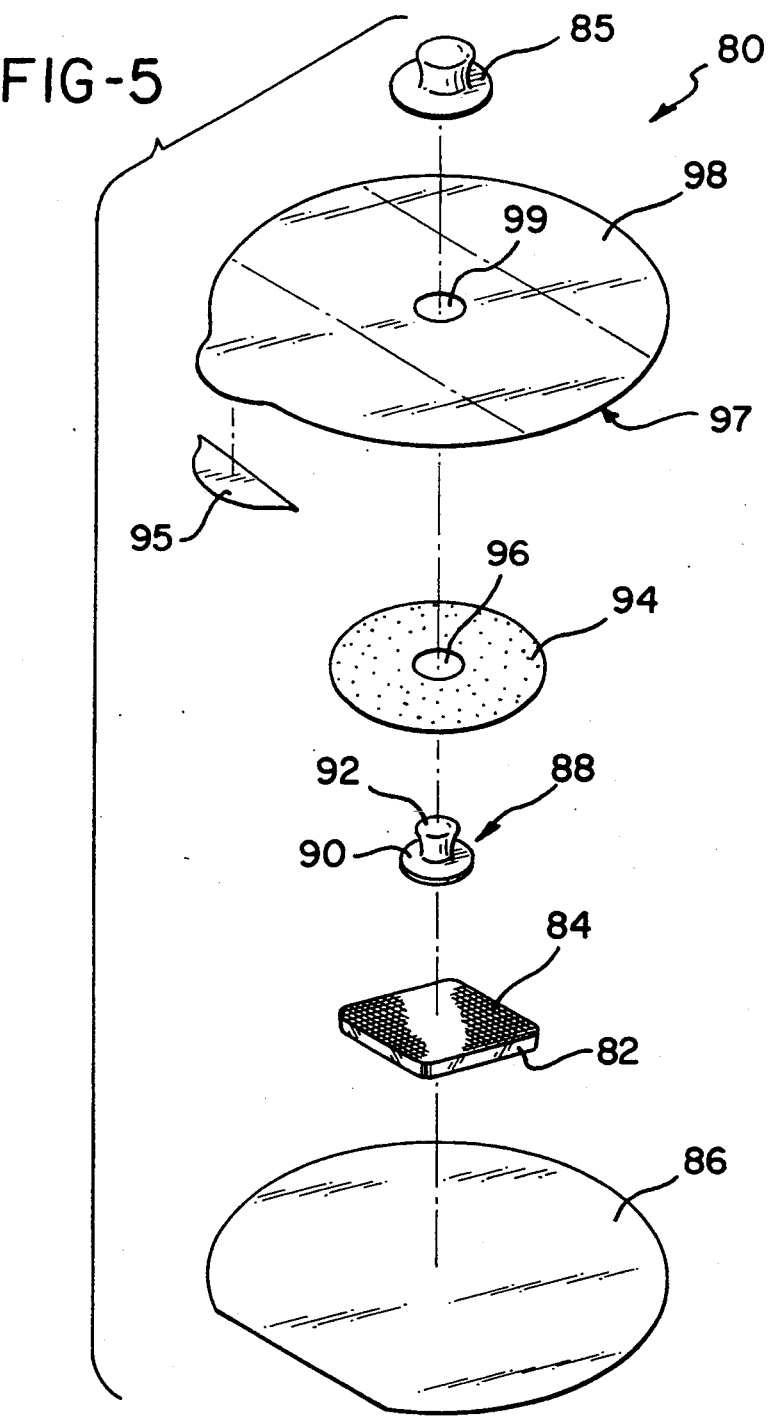
FIG. 5 is an exploded view of another embodiment of the biomedical electrode of the present invention.

FIG. 5 is an exploded perspective view of another embodiment of the invention in which a disposable biomedical electrode 80 as mounted on a release liner 86 prior to use. The biomedical electrode 80 comprises an electrolytic gel layer 82 having support layer 84 and first and second sides, wherein the first side is adapted to contact a patient. A conductive terminal 88 is included which has a base portion 90 integrally joined to a stud member 92, wherein the base portion 90 is centrally mounted to the second side of gel layer 82. The electrode 80 also includes an anchoring patch 94 having a first opening 96 correspondingly sized with the stud member 92 of the conductive terminal 88, wherein the anchoring patch 94 is mounted over the terminal 88 such that the stud member 92 protrudes through the opening 96 and the base portion 90 is held against the second side of gel layer 82.

The electrode 80 further comprises a top layer 98 having first and second sides and a second opening 99 correspondingly sized with the stud member 92 of the terminal 88. The anchoring patch 94 serves both to stabilize the terminal 88 and to reinforce top layer 98, thereby preventing terminal 88 from wiggling and obviating the need for a separate reinforcing strip. The second side of the top layer 98 has a patient-contact adhesive coating 97. The top layer 98 is adhesively mounted onto the anchoring patch 94 such that the stud member 92 protrudes through the second opening 99 and the periphery of the second side of the top layer 98 is capable of being secured to the patient. Finally, the electrode 80 includes a conductive cap portion 85. The cap portion 85 is positioned over the second opening 99 on the first side of the top layer 98 and is mounted to the stud member 92 of terminal 88. As such, cap portion 85 secures the terminal 88 to the top layer 98.

FIG. 5 also illustrates an optional conventional release tab 95 which can be secured to one portion of the lower side of the top layer 98. When the release tab 95 is used in conjunction with the release liner 86, the user can simply peel the electrode 80 from liner 86 by grasping the release tab 95. Thereafter, the user can remove the release tab 95 and mount the electrode 80 on the patient. Such techniques are conventional and well known. All materials used to make the various components of electrode 10 and electrode 50, as shown in FIGS. 1-2 and 3-4, respectively, can be used for the similar components of electrode 80.

Having described the invention in detail and by reference to preferred embodiments thereof, it will be apparent that modifications and variations are possible without departing from the scope of the invention which is defined in the appended claims.

What is claimed is:

1. A biomedical electrode comprising:
    an electrolytic gel layer having first and second sides wherein said first side is adapted to contact a patient;
    an anchoring layer having a perforated portion, a first side and a second side, and formed of a porous material having sufficient porosity such that said first side of said anchoring layer is secured to said second side of said gel layer;
    a conductive terminal having a base portion integrally joined to a stud member, said base portion being mounted on said perforated portion of said second side of said anchoring layer;
    a reinforcing strip having a first opening correspondingly sized with said stud member of said terminal, said reinforcing strip being mounted over said terminal such that said stud member protrudes through said first opening and said base portion is held against said second side of said anchoring layer; and
    a top layer having first and second sides and a second opening correspondingly sized with said stud member of said terminal, wherein said second side of said top layer has first and second ends and a patient-contact adhesive coating, said top layer being adhesively mounted onto said reinforcing strip and said anchoring layer such that said stud member protrudes through said second opening and said first and second ends of said second side of said top layer are capable of being secured to said patient.

2. The biomedical electrode of claim 1 wherein said porous material comprises a foam material including silica and a polyolefin.

3. The biomedical electrode of claim 1 wherein said porous material has a porosity in range from about 30% to about 80%.

4. The biomedical electrode of claim 1 further comprising a support layer disposed within said gel layer.

5. The biomedical electrode of claim 1 wherein said gel layer is a hydrogel material formed from an aqueous mixture of polyhydric alcohol, aliphatic diisocyanate-terminated prepolymer, polyethylene oxide-based polyamine, and sodium chloride.

6. The biomedical electrode of claim 1 wherein said gel layer is a hydrogel material formed from an aqueous mixture comprising:
    (a) from about 0% to about 90% by weight polyhydric alcohol;
    (b) from about 6% to about 60% by weight aliphatic diisocyanate-terminated prepolymer;
    (c) from about 4% to about 40% by weight polyethylene oxide-based polyamine;
    (d) 0% to about 2% by weight sodium chloride; and
    (e) the balance water.

7. The biomedical electrode of claim 6 wherein said polyhydric alcohol is selected from the group consisting of polypropylene glycol, polyethylene glycol and glycerine.

8. The biomedical electrode of claim 1 wherein said gel layer is a hydrogel material formed from an aqueous mixture comprising:
    (a) from about 15% to about 30% by weight polyhydric alcohol;
    (b) from about 8% to about 14% by weight isophoronediisocyanate-terminated prepolymer;
    (c) from about 5% to about 10% by weight polyethylene oxide-based diamine;
    (d) up to about 1% by weight sodium chloride; and
    (e) the balance water.

9. The biomedical electrode of claim 1 wherein said gel layer is a hydrogel material formed from an aqueous mixture comprising:
    (a) from about 16% to 17% by weight polypropylene glycol;
    (b) from about 10% to 12% by weight isophoronediisocyanate-terminated prepolymer;
    (c) from about 7% to 9% by weight polyethylene oxide-based diamine;
    (d) about 0.5% to 1% by weight sodium chloride; and
    (e) the balance water.

10. The biomedical electrode of claim 9 wherein said isophoronediisocyanate-terminated prepolymer is based on polyols containing more than about 40% polyethylene oxide and having an isocyanate content of about 3% by weight.

11. The biomedical electrode of claim 1 further comprising a release liner releasably secured to said first side of said gel layer for protection prior to use.

* * * * *